United States Patent [19]

Bauer et al.

[11] 4,026,929

[45] May 31, 1977

[54] SELECTIVE EXTRACTION OF GLYOXYLIC ACID FROM AQUEOUS MIXTURE WITH GLYOXAL

[75] Inventors: Kurt Bauer; Reiner Mölleken; Alfred Krempel, all of Holzminden, Germany

[73] Assignee: Haarmann & Reimer GmbH, Holzminden, Germany

[22] Filed: Dec. 29, 1975

[21] Appl. No.: 645,112

[30] Foreign Application Priority Data

Jan. 17, 1975 Germany .......................... 2501743

[52] U.S. Cl. ........................ 260/535 R; 260/530 R
[51] Int. Cl.$^2$ ......................................... C07C 59/30
[58] Field of Search ........ 260/535 R, 530 N, 530 R

[56] References Cited

UNITED STATES PATENTS 3,644,508  2/1972  Callighan et al. .............. 260/526 R Primary Examiner—Paul J. Killos
Attorney, Agent, or Firm—Burgess, Dinklage & Sprung

[57] ABSTRACT

Glyoxylic acid is selectively extracted from its aqueous mixture with glyoxal by means of aliphatic or cycloaliphatic alcohol containing about 4 to 8 carbon atoms, a ketone containing about 4 to 8 carbon atoms, and an ester of an aliphatic carboxylic acid and aliphatic alcohol each containing up to about 6 carbon atoms, the esters containing a total of about 3 to 8 carbon atoms, allowing the mixture to stratify and separating the solvent layer enriched in glyoxylic acid.

3 Claims, No Drawings

SELECTIVE EXTRACTION OF GLYOXYLIC ACID FROM AQUEOUS MIXTURE WITH GLYOXAL

This invention relates to a process for isolating glyoxylic acid from aqueous mixtures containing glyoxylic acid and glyoxal.

Glyoxal is used as a raw material in the plastics industry, in paper processing and in textile processing (see Chem. Week, 24.1 1973). Glyoxylic acid is used as an intermediate product, for example for the preparation of vanillin (see German Published Specification DOS 2,115,551).

Reaction mixtures containing glyoxylic acid and glyoxal are produced, for example, on reduction of oxalic acid or glyoxylic acid and especially on oxidation of acetaldehyde, ethylene, acetylene or ethylene glycol, above all on oxidation of acetaldehyde, ethylene or acetylene with nitric acid. The crude glyoxal solutions thereby produced contain varying amounts of by-products, for example also glyoxylic acid (see Ullmann, Enzykopadie der Technischen Chemie (Encyclopaedia of Industrial Chemistry), 1957, Volume 8, page 249).

Various processes for separating glyoxylic acid from glyoxal are already known. Thus, for example, German Published Specification DAS 1,198,339 recommends separating glyoxylic acid from glyoxal and the other products formed during the oxidation reaction, such as nitric acid and oxalic acid, by removing nitric acid and oxalic acid by means of a weak or medium-strength basic anion exchange resin and then separating the glyoxylic acid from glyoxal and the remaining impurities by crystallization after concentrating the solutions. According to the process described in German Published Specification DAS 1,154,081, aqueous solutions of dialdehydes, for example glyoxal, are freed from the by-products obtained in the process, such as glyoxylic acid, with the aid of anion exchange resins which contain secondary or tertiary amino groups or quaternary amino groups in the bicarbonate salt form [see also J. Appl. Chem. Biotechnol. 22 (1972) 1,243]. According to the process described in Polish Patent 57,126 [CA 71 (1969) 90,823], glyoxal from the reaction solutions produced by the oxidation of acetaldehyde or paraldehyde with nitric acid is separated from the reaction by-products, inter alia glyoxylic acid, in the form of its sodium bisulfite compounds. Japanese Published Patent 68/21-403 [CA 70 (1969) 77,318] described isolating glyoxal by electrodialysis from reaction mixtures, containing glyoxylic acid, resulting from the oxidation of acetaldehyde with nitric acid.

Attempts have also already been made to separate glyoxal and glyoxylic acid by extraction [see J. Appl. Chem. Biotechnol. 22 (1972) 1,243-1,252] but these experiments proved unsuccessful.

It is accordingly an object of the invention to provide a process for separating glyoxylic acid from aqueous solutions thereof also containing glyoxal.

This and other objects and advantages are realized in accordance with the present invention pursuant to which glyoxylic acid is selectively extracted from aqueous solutions thereof also containing glyoxal by means of aliphatic or cycloaliphatic alcohols containing about 4 to 8 carbon atoms, ketones containing about 4 to 8 carbon atoms or esters of aliphatic carboxylic acids and aliphatic alcohols each containing up to about 6 carbon atoms, the esters containing a total of 3 to about 8 carbon atoms.

The following may be mentioned as alcohols and ketones, containing 4 to 8 carbon atoms, which can be used according to the invention: 1-butanol, 2-butanol, 1-pentanol, 2-pentanol, 3-methyl-1-butanol, 1-hexanol, 1-heptanol, 2-heptanol, 2-butanone, 2-pentanone, 3-pentanone, 2-hexanone, 3-hexanone, 2-heptanone, 3-heptanone, cyclopentanol, methyl-cyclopentanol, cyclohexanol, methyl-cyclohexanol, cyclopentanone, cyclohexanone, and acetophenone.

The following may be mentioned as esters of aliphatic $C_1$-$C_6$-carboxylic acids and aliphatic $C_1$-$C_6$-alcohols which contain a total of 3–8 carbon atoms: acetic acid methyl ester, ethyl ester, propyl ester, butyl ester, pentyl ester and hexyl ester and propionic acid methyl ester, ethyl ester, propyl ester and butyl ester.

1-Butanol, 2-butanol, 1-pentanol, 2-pentanol, 3-methyl-1-butanol, 2-heptanol, cyclohexanol, cyclohexanone, acetic acid methyl ester and acetic acid ethyl ester have proved particularly suitable.

In some cases it can be advantageous to use mixtures of the above-mentioned solvents.

The extraction can be carried out in accordance with all extraction processes known industrially and in the laboratory. Preferably, the industrially customary counter-current extraction process is used.

Glyoxylic acid and glyoxal, and the by-products which may additionally be contained in the mixture, such as nitric acid, acetaldehyde and others, can be isolated from the solutions obtained in the process according to the invention in accordance with the customary enrichment processes, such as distilling off the solvents, re-extraction and the like.

In view of the past failure of extraction, it is surprising that an effective separation of glyoxylic acid from glyoxal is achieved by means of the extractants to be used according to the invention. Compared to the known processes of separation, the process according to the invention is distinguished by the fact that it is technically substantially simpler to carry out and results in complete separation of glyoxylic acid. Using the process according to the invention it proves possible to separate glyoxylic acid from glyoxal in a simple manner which can be carried out without difficulties even on an industrial scale.

The process is applicable to all aqueous solutions containing glyoxylic acid and glyoxal, especially to those containing from about 50 to 95% by weight of water and from about 5 to 50% by weight of the mixture of glyoxylic acid glyoxal whereby the minimum content for each of these compounds in the mixture is 3% by weight. It is obvious for those skilled in the art to choose a solvent with a low density or a high volume ratio to avoid phase-reversal, if solutions with a high content of the mixture of glyoxylic acid and glyoxal are to be extracted. Advantageously the volume ratio of extraction solvent to water is from 0,7 : 1 to 10 : 1 preferably from 0,7 : 1 to 5 : 1.

The invention will be further described in the following illustrative examples wherein all parts and percentages are by weight unless otherwise stated.

EXAMPLE 1

300 g. of a mixture of 20% of glyoxal, 15% of acetic acid, 5% of glyoxylic acid, 1% of nitric acid and 59% of water are initially introduced into a vertically arranged tube (1 = 80 cm, $\phi$ = 3 cm) having a P-1 frit insert at the lower end. 600 ml of ethyl acetate saturated with water are now metered hourly into the extraction tube from below, through the frit. After 13 hours the acid concentration, expressed as acetic acid, in the aqueous phase has fallen from originally 20% to 1.33%. After completion of the extraction, the glyoxal concentration in the aqueous solution (raffinate) is 20.9% and the nitric acid concentration is 0.17%.

The acid constituents, especially the acetic acid, are eluted from the organic phase with water. The glyoxylic acid can be separated off or isolated from the organic extract by evaporating the solvent, or as sodium glyoxylate.

EXAMPLE 2

10 g of a mixture of 15% of glyoxal, 15% of glyoxylic acid, 10% of acetic acid and 60% of water are subjected to a Craig distribution (counter current distribution; see e.g. Houben Weyl, Methoden der organischen Chemie, 4th Ed., 1958 Vol. I/1, pages 241 – 242 and 257 – 264) in an extraction apparatus comprising 33 stages. To do this, the mixture to be separated is introduced into element 1 and subjected to distribution using a volume ratio of solvent to water of 9 : 1, the solvent being a 1 : 1-mixture of ethyl acetate and methyl ethyl ketone saturated with water. Analysis of the aqueous (raffinate) phases and solvent phases gave the following distribution of the components:

Elements 1 – 3:
Combined raffinate phases: 1.3 g of glyoxal (no glyoxylic and acetic acid)

Elements 7 – 22:
Combined solvent phases: 0.6 g of glyoxylic acid. (no glyoxal and no acetic acid)

Elements 24 – 33:
Combined solvent phases: 0,98 g of acetic acid (no glyoxylic acid and no glyoxal)

The fractions not listed were discarded.

EXAMPLES 3 to 12

Aqueous solutions which contain, per liter, 55 g of glyoxylic acid and 220 g of glyoxal were extracted in a Craig extraction apparatus using various organic solvents.

The table which follows indicates the amount of aqueous solution employed, the solvents and amounts of solvents used for the extraction, the content of glyoxylic acid (A) and glyoxal (B) of the solvent phases and raffinate phases obtained, and the fractions ("isolated fractions") selected for determining the contents. The fractions not listed were discarded. The amounts of solvent in each case relate to one extraction stage. The data show that excellent separation of glyoxylic acid from glyoxal is achieved by means of the process according to the invention.

TABLE I

| Ex. | Amount of aqueous solution [liters] | Amount of organic solvent [liters] | Extraction stages | Isolated fractions | Solvent phase content of A = glyoxylic acid B = glyoxal | Isolated fractions | Raffinate phase content of A = glyoxylic acid B = glyoxal |
|---|---|---|---|---|---|---|---|
| 3 | 1.00 | Cyclohexanol 5 | 40 | 20 – 40 | A = 33.23g(= 94.9 %) B = 1.79g(= 5.1 %) | 1 – 19 | A = 0.61g(= 0.4 %) B = 144.92g(= 99.6 %) |
| 4 | 1.00 | Cyclohexanone 5 | 35 | 11 – 35 | A = 24.27g(= 98.3 %) B = 0.42g(= 1.7 %) | 1 – 10 | A = 0.63g(= 0.3 %) B = 187.03g(= 99.7 %) |
| 5 | 1.00 | Ethyl acetate 5 | 40 | 13 – 40 | A = 24.51g(= 96.3 %) B = 0.93g(= 3.7 %) | 1 – 13 | A = 1.33g (=11 0.7 %) B = 180.75g(= 99.3 %) |
| 6 | 0.5 | Acetophenone 2.5 | 85 | 19 – 85 | A = 7.08g(= 90.1 %) B = 0.78g(= 9.9 %) | 1 – 20 | A = 3.47g(= 3.6 %) B = 92.96g(= 96.4 %) |
| 7 | 0.5 | Hexyl acetate 2.8 | 85 | 10 – 85 | A = 3.79g(= 83.3 %) B = 0.76g(= 16.7 %) | 1 – 12 | A = 8.47g(= 7.7 %) B = 101.75g(= 92.3 %) |
| 8 | 0.5 | 2-Heptanol 3.05 | 40 | 24 – 40 | A = 19.70g(= 96.8 %) B = 0.65g(= 3.2 %) | 1 – 23 | A = 0.139g(= 0.2 %) B = 64.59g(= 99.8 %) |
| 9 | 1.00 | 2-Butanone 3.1 | 10 | 5 – 10 | A = 42.64g(= 100 %) B = 0.00g(= 0 %) | 1 – 2 | A = 0.001g(= 0 %) B = 217.78g(= 100 %) |
| 10 | 1.00 | n-Butanol 1.24 | 25 | 1 – 25 | A = 27.24g(= 99.99 %) B = 0.003g(= 0.01 %) | 1 – 6 | A = 0.07g(= 0.03 %) B = 202.56g(= 99.97 %) |
| 11 | 1.00 | 3-Methyl-1-butanol 6.17 | 25 | 21 – 25 | A = 52.24g(= 97.4 %) B = 1.42g(= 2.6 %) | 1 – 19 | A = 0.002g(= 0.0 %) B = 86.87g(=100 %) |
| 12 | 0.5 | 1-Pentanol 3.7 | 45 | 24 – 45 | A = 17.75g(= 94.1 %) B = 1.12g(= 5.9 %) | 1 – 23 | A = 0.20g(= 0.3 %) B = 67.40g(= 99.7 %) |

It will be appreciated that the instant specification and examples are set forth by way of illustration and not limitation, and that various modifications and changes may be made without departing from the spirit and scope of the present invention.

What is claimed is:

1. A process for isolating glyoxylic acid from an aqueous solution containing glyoxylic acid and glyoxal, comprising mixing the solution with at least one solvent selected from the group consisting of an aliphatic or cycloaliphatic alcohol containing about 4 to 8 carbon atoms, a ketone containing about 4 to 8 carbon atoms, and an ester of an aliphatic carboxylic acid and aliphatic alcohol each containing up to about 6 carbon atoms, the ester containing a total of about 3 to 8 carbon atoms, allowing the mixture to stratify and separating the solvent layer enriched in glyoxylic acid.

2. The process according to claim 1, wherein the solvent comprises at least one member selected from the group consisting of 1-butanol, 2-butanol, 1-pentanol, 2-pentanol, 3-methyl-1-butanol, 2-heptanol, cyclohexanol, acetic acid methyl ester, acetic acid ethyl ester and cyclohexanone.

3. The process according to claim 2, wherein the aqueous solution also contains acetic acid which preferentially enters the solvent layer along with the glyoxylic acid.

* * * * *